United States Patent
Wartini et al.

(10) Patent No.: US 7,301,058 B2
(45) Date of Patent: Nov. 27, 2007

(54) METHOD FOR INCREASING YIELD IN THE PRODUCTION OF POLYVALENT ALCOHOLS BY SPLITTING BY-PRODUCTS CONTAINING ACETAL

(75) Inventors: Alexander Wartini, Heidelberg (DE); Tilman Sirch, Schifferstadt (DE); Johann-Peter Melder, Böhl-Iggelheim (DE); Matthias Dernbach, Dossenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 499 days.

(21) Appl. No.: 10/521,810

(22) PCT Filed: Jul. 18, 2003

(86) PCT No.: PCT/EP03/07870

§ 371 (c)(1),
(2), (4) Date: Jan. 21, 2005

(87) PCT Pub. No.: WO2004/013074

PCT Pub. Date: Feb. 12, 2004

(65) Prior Publication Data

US 2005/0256346 A1    Nov. 17, 2005

(30) Foreign Application Priority Data

Jul. 26, 2002    (DE) ............................... 102 34 016

(51) Int. Cl.
C07C 31/18    (2006.01)
(52) U.S. Cl. ....................................... 568/853; 568/854
(58) Field of Classification Search ................ 568/853, 568/854
See application file for complete search history.

(56) References Cited

U.S. PATENT DOCUMENTS

| 4,122,290 A | 10/1978 | Immel et al. |
| 4,247,485 A | 1/1981 | Immel et al. |
| 6,096,905 A | 8/2000 | Supplee et al. |
| 6,187,971 B1 | 2/2001 | Kratz et al. |
| 6,448,457 B1 | 9/2002 | Hesse et al. |
| 6,586,641 B2 * | 7/2003 | Dernbach et al. ........... 568/853 |
| 2002/0189926 A1 | 12/2002 | Dernbach et al. |

FOREIGN PATENT DOCUMENTS

| DD | 287 251 | 2/1991 |
| DE | 25 07 461 | 9/1976 |
| DE | 27 02 582 | 7/1978 |
| DE | 28 13 201 | 10/1979 |
| DE | 198 09 418 A 1 | 9/1999 |
| DE | 199 63 435 A 1 | 7/2001 |
| EP | 1 178 030 A2 | 6/2002 |
| GB | 1291335 | 10/1972 |
| GB | 1 535 826 | 12/1978 |
| WO | WO 98/28253 | 7/1998 |

OTHER PUBLICATIONS

International Search Report dated Nov. 12, 2003, Int'l No. PCT/EP03/07870, 2 pages.

* cited by examiner

*Primary Examiner*—Elvis O. Price
(74) *Attorney, Agent, or Firm*—Connolly Bove Lodge and Hutz

(57) ABSTRACT

The invention relates to a method for increasing yield in the production of polyvalent alcohols, especially trimethylolpropane, obtained by condensing formaldehyde with a higher aldehyde. According to the inventive method, acid treatment is carried out on a mixture (high-boiling fraction) that is obtained by reprocessing, contains derivatives of said alcohols and has a higher boiling point than the respective alcohol, and the polyvalent alcohol is recovered from the acid-treated high-boiling fraction. The inventive method is characterised in that the water content of the high-boiling fraction amounts to between 20 and 90 wt. % in relation to the entire mixture of the high-boiling fraction and water.

20 Claims, No Drawings

METHOD FOR INCREASING YIELD IN THE PRODUCTION OF POLYVALENT ALCOHOLS BY SPLITTING BY-PRODUCTS CONTAINING ACETAL

RELATED APPLICATIONS

This application is a National Stage application of PCT/EP2003/007870 filed Jul. 18, 2003, which claims benefit to German application DE 102 34 016.1. filed Jul. 26, 2002.

The present invention relates to a process for increasing the yield in preparing polyhydric alcohols (obtained by condensing formaldehyde with a higher aldehyde) by decomposing acetals formed in the preparation, by acid treatment in a high boiler fraction having a water content of from 20 to 90% by weight obtained by a workup.

Polyhydric alcohols are obtained on a large scale by condensing formaldehyde with higher, CH-acidic aldehydes or with water and acrolein or 2-alkylacrolein. In this reaction, a distinction is drawn between two principal operational variants.

On the one hand, there is the Cannizarro process which is divided in turn into the inorganic and the organic Cannizzaro process. In the inorganic variant, an excess of formaldehyde is reacted with the appropriate alkanal in the presence of stoichiometric amounts of an inorganic base such as NaOH or Ca(OH)$_2$. The methylol alkanal formed in the first stage reacts in the second stage with the excess formaldehyde in a disproportionation reaction to give the polyhydric alcohol and the formate of the appropriate base, i.e. sodium formate or calcium formate. The occurrence of these salts is a disadvantage, since they are difficult to remove from the reaction product, and one equivalent of formaldehyde is also lost.

In the organic Cannizzaro process, a tertiary alkylamine is used instead of an inorganic base. Trialkylammonium formate occurs as an undesired by-product. One equivalent of formaldehyde is therefore also lost in this process.

The disadvantages of the Cannizzaro process are avoided by the hydrogenation process. Formaldehyde is reacted with the appropriate aldehyde in the presence of catalytic amounts of an amine. This achieves the stopping of the reaction at the stage of the alkylolated aldehyde. After removal of the formaldehyde, the reaction mixture which, as well as the alkylolated aldehyde mentioned, still contains small amounts of the appropriate polyhydric alcohol and of acetals of the alcohols formed is subjected to a hydrogenation in which the desired polyhydric alcohol is obtained.

A particularly effective process for preparing alcohols obtainable by condensing aldehydes with formaldehyde is described in WO 98/28253. This process makes it possible to achieve high yields combined with the occurrence of small amounts of coproducts. The procedure is to react the higher aldehyde with from 2 to 8 times the amount of formaldehyde in the presence of a tertiary amine and to separate the reaction mixture obtained in this way into two solutions, one of which comprises the completely methylolated alkanal mentioned and the other comprises unconverted starting product. This latter solution is recycled into the reaction. The separation is effected by distillation or simple removal of the aqueous phase from the organic phase. The solution comprising the product is subjected to a catalytic and/or thermal treatment in order to convert incompletely alkylolated alkanals to the desired completely methylolated compounds. By-products formed are removed by distillation and the resulting bottom product is fed to the catalytic hydrogenation which leads to the polyhydric alcohols.

Examples of important alcohols prepared by the process as described include neopentyl glycol, pentaerythritol, trimethylolethane, trimethylolbutane and in particular trimethylolpropane (TMP).

The alcohols prepared by both the Cannizzaro and the hydrogenation process have to be freed distillatively of components which are more volatile (low boilers) and less volatile (high boilers) than them and also of components which boil in the region of the alcohol (medium boilers). Low boilers are in particular water, methanol and, when using an amine as catalyst, the free amine.

The high boilers and medium boilers are often compounds which are derivatives of the polyhydric alcohol prepared and result from it by reaction with, for example, formaldehyde, methanol or else an aldehyde or alkanol formed in the course of the process.

For the use of the polyhydric alcohol, a low formaldehydic acetal content in particular of the alcohol is significant.

Formaldehydic acetals are all compounds which are derived from formaldehyde and have the structural element

and may also be referred to as formals.

In the preparation of polyhydric alcohols, formaldehydic acetals of the general formulae (IIa) or (IIb)

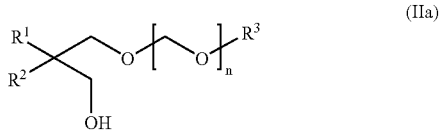

occur, where
R$^1$, R$^2$ are each independently hydrogen, C$_1$- to C$_{10}$-alkyl, C$_1$- to C$_{10}$-hydroxyalkyl, carboxyl or C$_1$- to C$_4$-alkoxycarbonyl, preferably C$_1$- to C$_{10}$-alkyl and C$_1$- to C$_{10}$-hydroxyalkyl,
R$^3$ is hydrogen, C$_1$- to C$_{10}$-alkyl, preferably C$_1$- to C$_8$-, more preferably C$_1$- to C$_5$-alkyl, or C$_1$- to C$_{10}$-hydroxyalkyl, preferably C$_1$- to C$_8$-alkyl, more preferably C$_1$- to C$_5$-alkyl, and
n is an integer from 1 to 4, preferably from 1 to 3 and more preferably from 1 to 2, and the alkyl radicals may each be branched or unbranched.

Examples of R$^1$ and R$^2$ include hydrogen, methyl, ethyl, iso-propyl, n-propyl, n-butyl, iso-butyl, sec-butyl, tert-butyl, n-pentyl, n-hexyl, n-heptyl, n-octyl, n-decyl, hydroxymethyl, carboxyl, methoxycarbonyl, ethoxycarbonyl or n-butoxycarbonyl, preferably hydrogen, hydroxymethyl, methyl and ethyl, more preferably hydroxymethyl, methyl and ethyl.

Examples of R$^3$ include hydrogen, methyl, ethyl, n-propyl, n-butyl, 2-methylpropyl, 2-methylbutyl, 2-ethyl-3-hydroxypropyl, 2-methyl-3-hydroxypropyl, 2,2-bis(hydroxymethyl)butyl, 2,2-bis(hydroxymethyl)propyl, 2,2- dimethyl-3-hydroxypropyl, 3-hydroxypropyl, 3-hydroxy-2-(hydroxymethyl)propyl or 3-hydroxy-2,2-bis(hydroxymethyl)propyl.

Examples of typical formaldehydic acetals in the case of the synthesis of the trihydric alcohol trimethylolpropane (TMP) from formaldehyde and n-butyraldehyde in the presence of catalytic amounts of trialkylamine are the TMP-formaldehyde-methanol acetals (IIIa) and (IIIb) mentioned below, from 0.05 to 10% by weight of which may be present in the crude product of the hydrogenation process

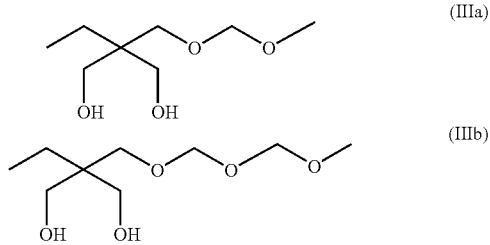

and also the linear bis-TMP formal [C$_2$H$_5$C(CH$_2$OH)$_2$ CH$_2$O]$_2$CH$_2$ (IV) and the cyclic TMP formal

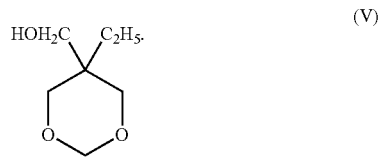

It is obvious that the formation of these acetals comprising units of the polyhydric alcohol, in particular TMP units, is undesired, since they distinctly reduce the yield of desired product and, in addition, adversely affect the application properties of the product alcohol. In order to avoid these disadvantages, it is desirable to cleave the formaldehydic acetals and recover the TMP units. The literature discloses various methods of achieving this.

U.S. Pat. No. 6,096,905 discloses a process in which a composition obtained by the Cannizarro process and comprising the linear bis-TMP formal or the linear bis-trimethylolethane formal is treated with a strong acid catalyst at from 30 to 300° C. for from ½ to 8 hours. The treated composition should not contain more than 15% by weight of water. The addition of a hydrocarbon which forms an azeotrope with water is recommended in order to keep the water content low.

DD-A 287 251 discloses the recovery of trimethylolpropane from by-products having higher boiling points than trimethylolpropane by acid cleavage. The preparation of trimethylolpropane described is by the Cannizarro process. Therefore a maximum content of alkali metal or alkaline earth metal compounds for the acid cleavage of 0.05 kg/kg is specified. As in U.S. Pat. No. 6,096,905, DD-A 287 251 also recognizes the water concentration in the acidic cleavage of the high-boiling by-products as a critical quantity for the conversion. DD 287 251 recommends a very low water content, but a maximum of 0.05 kg/kg.

A disadvantage of both prior art processes is that the strong acidic medium may lead to secondary reactions which may have a disadvantageous influence on the properties of the desired polyhydric alcohol, such as the color number.

It is an object of the present invention to provide a process which allows the yield losses in the preparation of polyhydric alcohols, in particular TMP, preferably by the hydrogenation process, to be reduced by the formation of high-boiling TMP-containing by-products. The process should be effective and not costly or inconvenient, but at the same time allow the yield of polyhydric alcohol to be improved to such an extent that it is worth using in particular in the hydrogenation process.

We have found that this object is achieved by a process for increasing the yield in preparing polyhydric alcohols, in particular trimethylolpropane, obtained by condensing formaldehyde with a higher aldehyde, by acid treatment of a mixture (high boiler fraction) comprising derivatives of these alcohols obtained by workup and having a higher boiling point than the particular alcohol and recovery of the polyhydric alcohol from the acid-treated high boiler fraction, wherein the water content of the high boiler fraction is from 20 to 90% by weight, preferably from 40 to 80% by weight and particularly preferably from 70 to 75% by weight, based on the total amount of high boiler fraction and water.

It has been found that, surprisingly, when the water content of the fraction comprising the high-boilers is high, it is possible to achieve an effective decomposition of the particular high-boiling derivative and thus to distinctly increase the yield. This simple process results in a yield increase which may be up to several percent.

In the process according to the invention, the polyhydric alcohol may have been synthesized either by the Cannizarro or by the hydrogenation process.

The synthesis mixture obtained by the Cannizarro process is customarily worked up by initially neutralizing the inorganic or organic base such as NaOH, Ca(OH)$_2$ or tertiary alkylamine serving as catalyst and removing excess aldehyde. The polyhydric alcohol is then separated from the formate of the inorganic or organic base and from water (low boilers). As well as compounds of the base used as catalyst, for example salts such as formates, the crude product obtained which comprises the polyhydric alcohol also comprises by-products such as acetals and esters and other compounds having higher boiling points than the polyhydric alcohol. These by-products are customarily separated from the main product by distillation to give a fraction having a higher boiling point than the polyhydric alcohol (high boiler fraction) and a more volatile fraction (medium boiler). The process according to the invention recovers the bonded units of the polyhydric alcohol in a gentle and effective manner from this high boiler fraction which is obtained by the workup known per se and comprises compounds having higher boiling points than the polyhydric alcohol such as the abovementioned formaldehydic acetals of the general formulae (IIa) and (IIb).

However, preference is given to using the process according to the invention on high-boiler fractions obtained from synthesis mixtures of the hydrogenation process by workup. The polyhydric alcohol is prepared in the hydrogenation process as described in the literature by aldolizing formaldehyde with a higher aldehyde in the presence of catalytic amounts of a tertiary amine and hydrogenating the resulting mono- or polymethylolalkanals, preferably of dimethylolbutanal to trimethylolpropane.

Examples of various process variants can be found in the applications DE-A-25 07 461, DE-A-27 02 582 and DE-A-

28 13 201 which have already been cited above. The process according to the invention is particularly suitable for increasing the yield in synthesis mixtures which have been prepared by the process described in WO 98/28253. A short description of this process can be found above. The workup is effected in a customary manner, as described in the literature, generally by removal of water and subsequent distillation. The high-boiler fraction can be removed in the workup from product and medium boilers, for example by distillation. In a separate stage, the high boiler fraction is then used to carry out the process according to the invention and the product alcohol obtained by the decomposition of the high boilers is distilled off.

The process according to the invention for increasing the yield can be carried out particularly efficiently using a high boiler fraction obtained by the process described in DE-A 199 63 435. The disclosure content of the application mentioned is incorporated in the present application by way of reference.

In the process disclosed in DE-A 199 63 435, polyhydric alcohol obtained by hydrogenating mono- or polymethylolalkanols, in particular trimethylolpropane (TMP) obtained from 2,2-dimethylolbutanol, is worked up distillatively to remove water and other low boilers such as methanol, trialkylamine and trialkylammonium formate in the first stage by distillation from the crude product obtained after the hydrogenation.

The majority of the polyhydric alcohol, in particular TMP, and the medium boilers are separated distillatively from the high boilers in the mixture obtained in the first stage as a bottom product which comprises the polyhydric alcohol, in particular TMP, high boilers and a portion of the compounds having lower boiling points than the polyhydric alcohol, for example TMP formate, ethylpropanediol and cyclic TMP formal (referred to hereinbelow as medium boilers). The high boiler fraction is then treated with acid in the process according to the invention.

The pure polyhydric alcohol is recovered from the fraction comprising the majority of the polyhydric alcohol and the medium boilers with the removal of the medium boilers and may optionally be subjected to a further purifying distillation to recover polyhydric alcohol having a low color number.

The product alcohol may be recovered from the high boiler fraction after the acid treatment according to the invention of product alcohol, preferably by distillation. However, in a particularly preferred embodiment of the process according to the invention, some or all of the acid-treated high boiler fractions are recycled directly to the hydrogenation stage of the hydrogenation process, i.e. to the hydrogenation of the mono- or polymethylolalkanals to the polyhydric alcohol, in particular of dimethylolbutanal to TMP. When some of the acid-treated high boiler fraction is recycled, high-boiling by-products are removed from it before recycling using a distillative separating device or a phase separator. The removed by-products may be, for example, incinerated or disposed of in another way.

This procedure offers the advantage over the direct removal of the product alcohol from the acid-treated high-boiler fraction that it avoids the reforming of high-boiling acetals by transacetalization of the aldehydes formed by the hydrogenation and therefore makes it possible to achieve yield increases in the region of several percent.

In a particular embodiment, some or all of the medium boiler fraction removed from the majority of the polyhydric alcohol may also be recycled and subjected to the acid treatments mixed with the high boiler fraction. This mixing with the medium boiler fraction leads to a further yield increase by the cleavage of medium-boiling acetals. It would also be possible to treat the medium boiler fraction instead of the high boiler fraction by the process according to the invention. However, it was determined according to the invention that the treatment of the high boiler fraction itself or mixed with the medium boilers is advantageous.

According to the invention, it has been recognized that water contents of the high boiler fraction of from 20 to 90% by weight, preferably from 40 to 80% by weight, more preferably from 70 to 75% by weight, make it possible to particularly effectively recover polyhydric alcohol, in particular TMP, from the high boiler fraction. The water contents according to the invention can be attained by adding water.

The amount of acid which is added to the mixture in the present invention to decompose the high boilers is, according to the invention, from 0.1 to 20% by weight, based on the total amount of high boiler fraction and water, or the mixture of high boiler fraction and medium boiler fraction and water, preferably from 0.1 to 10% by weight, more preferably from 0.5 to 2.5% by weight.

According to the invention, useful acids include $C_1$- to $C_{12}$-carboxylic acids such as formic acid, acetic acid, propionic acid, butyric acid, 2-ethylhexanoic acid and lactic acid, $C_2$- to $C_{12}$-dicarboxylic acids such as oxalic acid, malonic acid, maleic acid, succinic acid and tartaric acid, sulfonic acids, mineral acids such as sulfuric acid, phosphoric acid and sulfurous acid, acidic gases in gaseous or aqueous form such as carbon dioxide or sulfur dioxide or acidic ion exchangers. Preference is given to using formic acid and phosphoric acid. Particular preference is given to using formic acid.

According to the invention, it has been recognized that formic acid is particularly suitable. This is surprising, since, in contrast to the mineral acid, formic acid forms TMP esters and these TMP formates can only be removed from the polyhydric alcohol with difficulty.

Particularly in the particular embodiment of the process according to the invention described above in which some or all, preferably all, of the acid-treated high boiler fraction is recycled into the hydrogenation, the advantages of formic acid can be fully utilized, since the hydrogenation catalysts used with preference in the hydrogenation process for preparing polyhydric alcohols are capable of cleaving formates. Such hydrogenation catalysts are disclosed, for example in DE 101 52 527.7 "Decomposition of ammonium formates in polyolic reaction mixtures" whose disclosure content is explicitly incorporated herein by way of reference.

In a particularly preferred embodiment, the hydrogenation is carried out in the presence of the catalyst which is disclosed by DE-A 198 09 418 (which is explicitly incorporated herein by way of reference) and comprises an inorganic support comprising $TiO_2$ and, as active component, copper or a mixture of copper with at least one of the metals selected from the group of zinc, aluminum, cerium, a nobel metal and a metal of transition group VIII and has a maximum specific copper surface area of 10 $m^2/g$. The support of these catalysts is preferably $TiO_2$ or a mixture of $TiO_2$ and $Al_2O_3$ or a mixture of $TiO_2$ and $ZrO_2$ or a mixture of $TiO_2$, $Al_2O_3$ and $ZrO_2$, and particular preference is given to using $TiO_2$. When preparing this catalyst according to DE-A 19809418, metallic Cu powder may be added as a further additive during the tableting, so that the maximum copper surface area is 10 $m^2/g$.

The acid treatment according to the invention of the high boiler fraction takes place at temperatures of from 30 to 180° C., preferably from 80 to 120° C. Residence times based on the high boiler fraction are chosen which range from 0.5 to 10 hours, preferably from 1 to 6 hours.

The process according to the invention is not markedly pressure-dependent. The decomposition may be carried out under reduced pressure, under atmospheric pressure or else with the application of an external pressure, but preferably under atmospheric pressure or under the autogenous pressure of the system. Operation may be effected without an inert gas atmosphere, or with one, for example an argon or nitrogen atmosphere.

The process is applicable to all polyhydric alcohols which may be prepared by condensing formaldehyde with higher aldehydes with the addition of catalytic amounts of trialkylamine and subsequent hydrogenation. Useful higher aldehydes are virtually all alkanals having an acidic hydrogen atom in the α-position to the carbonyl group. Aliphatic aldehydes having from 2 to 24 carbon atoms may be used as starting materials and may be straight-chain or branched or else contain alicyclic groups. Equally, araliphatic aldehydes are suitable as starting materials, provided that they contain a methylene group in the α-position to the carbonyl group. In general, aralkylaldehydes having from 8 to 24 carbon atoms, preferably from 8 to 12 carbon atoms, are used as starting materials, for example phenylacetaldehyde. Preference is given to aliphatic aldehydes having from 2 to 12 carbon atoms, for example 3-ethyl-, 3-n-propyl-, 3-isopropyl-, 3-n-butyl-, 3-isobutyl-, 3-sec-butyl- or 3-tert-butylbutanal and also corresponding n-pentanals, n-hexanals and n-heptanals; 4-ethyl-, 4-n-propyl-, 4-isopropyl-, 4-n-butyl-, 4-isobutyl-, 4-sec-butyl-, 4-tert-butylpentanals, n-hexanals, n-heptanals; 5-ethyl-, 5-n-propyl-, 5-isopropyl-, 5-n-butyl-, 5-isobutyl-, 5-sec-butyl-, 5-tert-butyl-n-hexanals or -n-heptanals; 3-methylhexanal, 3-methylheptanal; 4-methylpentanal, 4-methylheptanal, 5-methylhexanal, 5-methylheptanal; 3,3,5-trimethyl-n-pentyl-, 3,3-diethylpentyl-, 4,4-diethylpentyl-, 3,3-dimethyl-n-butyl-, 3,3-dimethyl-n-pentyl-, 5,5-dimethylheptyl-, 3,3-dimethylheptyl-, 3,3,4-trimethylpentyl-, 3,4-dimethylheptyl-, 3,5-dimethylheptyl-, 4,4-dimethylheptyl-, 3,3-diethylhexyl-, 4,4-dimethylhexyl-, 4,5-dimethylhexyl-, 3,4-dimethylhexyl-, 3,5-dimethylhexyl-, 3,3-dimethylhexyl-, 3,4-diethylhexyl-, 3-methyl-4-ethylpentyl, 3-methyl-4-ethylhexyl-, 3,3,4-trimethylpentyl-, 3,4,4-trimethylpentyl-, 3,3,4-trimethylhexyl-, 3,4,4-trimethylhexyl-, 3,3,4,4-tetramethylpentylaldehyde; in particular $C_2$ to $C_{12}$-n-alkanals.

For the purposes of the present invention, particularly preferred polyhydric alcohols are trimethylolethane, trimethylolpropane, trimethylolbutane, neopentyl glycol and pentaerythritol. The most preferred alcohol is trimethylolpropane.

The invention is now illustrated in the following examples.

EXAMPLES

Example 1

Preparation of Crude TMP

Crude TMP was prepared as follows:
An apparatus consisting of two heatable stirred tanks connected to one another via overflow pipes and having a total capacity of 72 l was continuously charged with fresh, aqueous formaldehyde solution (4300 g/h) in the form of the 40% aqueous solution and n-butyraldehyde (1800 g/h) and with fresh trimethylamine as catalyst (130 g/h) in the form of the 45% aqueous solution. The reactors were heated to 40° C.

The effluent was passed directly into the upper section of a falling-film evaporator having a fitted column and distillatively separated there at atmospheric pressure into a low-boiling top product substantially comprising n-butyraldehyde, ethylacrolein, formaldehyde, water and trimethylamine and a high-boiling bottom product.

The top product was condensed continuously and recycled into the above-described reactors.

The high-boiling bottom product from the evaporator (about 33.5 kg/h) was continuously admixed with fresh trimethylamine catalyst (50 g/h, in the form of the 45% aqueous solution) and conducted into a heatable tubular reactor having a capacity of 12 l and provided with a random packing. The reactor was heated to 40° C.

The effluent of the postreactor was conducted continuously into the upper section of a further distillation device, the formaldehyde removal, and distillatively separated there into a low-boiling top product substantially comprising ethylacrolein, formaldehyde, water and trimethylamine, and a high-boiling bottom product. The low-boiling top product (27 kg/h) was continuously condensed and recycled into the first stirred tank, whereas the high-boiling bottom product was collected.

As well as water, the bottom product obtained in this way substantially comprised dimethylolbutyraldehyde, formaldehyde and traces of monomethylolbutyraldehyde. It was then subjected to a continuous hydrogenation. To this end, the reaction solution was hydrogenated at 90 bar and 115° C. in a main reactor by the cycle/trickle method and a downstream postreactor by the cycle method. The catalyst was prepared in a similar manner to DE 198 09 418. It contained 24% of CuO, 20% of Cu and 46% of $TiO_2$. The apparatus used consisted of a 10 m long heated postreactor (internal diamter: 25 mm). The cycle throughput was 25 l/h of liquid, and the reactor feed was set to 4 kg/h. Accordingly, 4 kg/h of hydrogenation effluent were obtained.

The mixture obtained after the hydrogenation was worked up distillatively by the method described in examples 2 and 3 of DE 199 63 435.

In this method, the mixture obtained after a water removal is separated into a fraction having a higher boiling point than TMP, referred to here as high boiler fraction, and a fraction having a lower boiling point than TMP, referred to here as medium boilers.

The high boiler fraction obtained in this manner is composed substantially of the following compounds: 45% of TMP-DMB acetal, 10% of linear bis-TMP formal (IV), 10-25% of TMP and 20-35% of unknown high boilers.

The medium boiler fraction obtained is composed substantially of the following compounds: 50% consist of TMP and TMP formate, 10% of the cyclic TMP formal (V), 5-10% of TMP-formaldehydeacetals (IIa), 5% of 2-ethylpropanediol and about 20% are unknown medium boilers.

Examples 2 to 11

All experiments up to 100° C. were carried out in a stirred apparatus at atmospheric pressure under nitrogen. Experiments above 100° C. were carried out in an autoclave under nitrogen pressure (50 bar).

The analysis was effected with the aid of gas chromatography (GC) using a J&W Scientific DB5 column (30 m, 0.32 mm, 1 μm), injector: 300° C., 90° C. at 15 K per minute. The detection was effected with an FID.

Examples 2 to 9

100 g of high boiler fraction prepared as described in example 1 was admixed with the amount of water and formic acid described in table 1 and heated to the specified temperature with stirring and under protective gas. At temperatures above 100° C., the reaction was carried out in an autoclave. The pH in all experiments was from 2 to 3. The increases in dimethylolbutanol (DMB) and trimethylolpropane (TMP) were determined by gas chromatography and, based on a comparison with the same amount of water without acid under otherwise identical reaction conditions, are quoted as yield increases in GC area-%. The results are summarized in table 1.

TABLE 1

| No. | Temp. [° C.] | Exp. time [h] | Amount of water [g] | Amount of water [% by wt.][1] | Amount of HCOOH [% by wt.][1] | Increase in DMB [GC area-%] | Increase in TMP [GC area-%] |
|---|---|---|---|---|---|---|---|
| 2 | 80  | 6 | 0   | 0  | 5.0  | 0   | −3.3 |
| 3 | 120 | 4 | 0   | 0  | 5.0  | 0   | −6.4 |
| 4 | 100 | 6 | 100 | 50 | 10.0 | 3.4 | 7.3  |
| 5 | 100 | 6 | 100 | 50 | 2.5  | 4.1 | 18.9 |
| 6 | 100 | 6 | 30  | 23 | 2.5  | 2.6 | 5.5  |
| 7 | 100 | 6 | 70  | 41 | 2.5  | 3.6 | 15.8 |
| 8 | 100 | 6 | 300 | 75 | 1.0  | 9.4 | 31.8 |
| 9 | 100 | 6 | 500 | 83 | 1.0  | 5.3 | 36.3 |

[1]% by weight are based on the total amount of high boiler fraction and water

Example 10

100 g of medium boiler fraction obtained as in example 1 were admixed with the amounts of water and formic acid described in the table and heated to the specified temperature with stirring and under protective gas. The evaluation by GC analysis shows the rise in trimethylolpropane (TMP) and 2,2'-dimethylbutanal (DMB). The pH was 2.4. The result is summarized in table 2.

TABLE 2

| No. | Temp. [° C.] | Exp. time [h] | Amount of water [g] | Amount of water [% by wt.][1] | Amount of HCOOH [% by wt.][1] | Increase in DMB [GC area-%] | Increase in TMP [GC area-%] |
|---|---|---|---|---|---|---|---|
| 10 | 100 | 6 | 100 | 50 | 1.0 | 0 | 25.9 |

[1]% by weight are based on the total amount of high boiler fraction and water

Example 11

50 g of high boiler fraction were mixed with 50 g of medium boiler fraction, each obtained as described in example 1. The mixture was admixed with the amount of water and formic acid described in table 3 and heated to the specified temperature with stirring and under protective gas. The evaluation by GC analysis shows the rise of trimethylolpropane (TMP) and 2,2'-dimethylbutanal (DMB). The pH is 2.1.

TABLE 3

| No. | Temp. [° C.] | Exp. time [h] | Amount of water [g] | Amount of water [% by wt.][1] | Amount of HCOOH [% by wt.][1] | Increase in DMB [GC area-%] | Increase in TMP [GC area-%] |
|---|---|---|---|---|---|---|---|
| 11 | 100 | 6 | 300 | 75 | 1.0 | 3.9 | 15.1 |

[1]% by weight are based on the total amount of high boiler fraction and water

We claim:
1. A process for preparing polyhydric alcohols in increased yields comprising aldolizing formaldehyde with a higher aldehyde in the presence of catalytic amounts of a tertiary amine and hydrogenating the resulting mono- or polymethylolalkanals, said process further comprising the steps of:

a) distillative removal of components having lower boiling points than the polyhydric alcohol from the crude product of the hydrogenation of the mono- or polymethylolalkanals;

b) separation of the resulting bottom product in a second distillation stage into a high boiler fraction and a fraction comprising the majority of the polyhydric alcohol;

c) acid treatment of the high boiler fraction, the water content of the high boiler fraction being from 20% to 90% by weight, based on the total amount of high boiler fraction and water; and d) distillation of the fraction comprising the majority of the polyhydric alcohol to remove the more volatile compounds (medium boiler fraction) and recovery of pure polyhydric alcohol;

wherein the acid-treated high boiler fraction is recycled into the hydrogenation of the mono- or polymethylolalkanals to the polyhydric alcohol.

2. The process according to claim 1, wherein some or all of the medium boiler fraction removed from the fraction comprising the majority of the polyhydric alcohol by distillation is mixed with the high boiler fraction before the acid treatment.

3. The process according to claim 1, wherein the acid concentration is from 0.1% by weight to 20% by weight, based on the total amount of high boiler fraction or the mixture of high boiler fraction and middle boiler fraction and water.

4. The process according to claim, wherein the acid is selected from the group consisting of $C_1$- to $C_{12}$-carboxylic acids, $C_2$- to $C_{12}$-dicarboxylic acids, sulfonic acids, mineral acids, carbon dioxide, sulfur dioxide and acidic ion exchangers.

5. The process according to claim 1, wherein formic acid is used.

6. The process according to claim 1, wherein the polyhydric alcohols are selected from the group consisting of trimethylolethane, trimethylolpropane, trimethylolbutane, neopentyl glycol and pentaerythritol.

7. The process according to claim 1, wherein the polyhydric alcohol is trimethylolpropane.

8. The process according to claim 2, wherein the acid concentration is from 0.1% by weight to 20% by weight, based on the total amount of high boiler fraction or the mixture of high boiler fraction and middle boiler fraction and water.

9. The process according to claim 2, wherein the acid is selected from the group consisting of $C_1$- to $C_{12}$-carboxylic acids, $C_2$- to $C_{12}$-dicarboxylic acids, sulfonic acids, mineral acids, carbon dioxide, sulfur dioxide and acidic ion exchangers.

10. The process according to claim 3, wherein the acid is selected from the group consisting of $C_1$- to $C_{12}$-carboxylic acids, $C_2$- to $C_{12}$-dicarboxylic acids, sulfonic acids, mineral acids, carbon dioxide, sulfur dioxide and acidic ion exchangers.

11. The process according to claim 8, wherein the acid is selected from the group consisting of $C_1$- to $C_{12}$-carboxylic acids, $C_2$- to $C_{12}$-dicarboxylic acids, sulfonic acids, mineral acids, carbon dioxide, sulfur dioxide and acidic ion exchangers.

12. The process according to claim 2, wherein formic acid is used.

13. The process according to claim 2, wherein the polyhydric alcohols are selected from the group consisting of trimethylolethane, trimethylolpropane, trimethylolbutane, neopentyl glycol and pentaerythritol.

14. The process according to claim 3, wherein the polyhydric alcohols are selected from the group consisting of trimethylolethane, trimethylolpropane, trimethylolbutane, neopentyl glycol and pentaerythritol.

15. The process according to claim 4, wherein the polyhydric alcohols are selected from the group consisting of trimethylolethane, trimethylolpropane, trimethylolbutane, neopentyl glycol and pentaerythritol.

16. The process according to claim 5, wherein the polyhydric alcohols are selected from the group consisting of trimethylolethane, trimethylolpropane, trimethylolbutane, neopentyl glycol and pentaerythritol.

17. The process according to claim 2, wherein the polyhydric alcohol is trimethylolpropane.

18. The process according to claim 3, wherein the polyhydric alcohol is trimethylolpropane.

19. The process according to claim 4, wherein the polyhydric alcohol is trimethylolpropane.

20. The process according to claim 5, wherein the polyhydric alcohol is trimethylolpropane.

* * * * *